United States Patent [19]

Maignan et al.

[11] Patent Number: 4,980,509
[45] Date of Patent: Dec. 25, 1990

[54] NEW AROMATIC POLYCYCLIC DERIVATIVES, THEIR PROCESS OF PREPARATION AND THEIR USE IN HUMAN AND VETERINARY MEDICINE AND IN COSMETICS

[75] Inventors: Jean Maignan, Tremblay Les Gonesse; Gérard Lang, Saint Gratien; Gérard Malle, Villiers Sur Morin; Serge Restle, Aulnay-sous-Bois, all of France

[73] Assignee: Societe Anonyme dite: L'Oreal, Paris, France

[21] Appl. No.: 214,225

[22] Filed: Jul. 1, 1988

[30] Foreign Application Priority Data

Jul. 3, 1987 [FR] France .................. 87 09478

[51] Int. Cl.$^5$ .......................................... C07C 315/00
[52] U.S. Cl. ...................................... 568/28; 568/27; 568/30; 568/31; 568/32
[58] Field of Search .............. 424/70; 568/28, 27, 568/30, 31, 32; 260/397.6; 564/80

[56] References Cited

U.S. PATENT DOCUMENTS

| 3,655,772 | 4/1972 | Chang et al. ................. 568/30 |
| 3,848,000 | 11/1974 | Chabardes et al. ............ 568/28 |
| 3,960,967 | 6/1976 | Olson et al. .................. 568/30 |
| 4,049,718 | 9/1977 | Chabardes et al. ............ 568/28 |

FOREIGN PATENT DOCUMENTS 2164644 3/1986 United Kingdom .
2164938 4/1986 United Kingdom .

Primary Examiner—Merrell C. Cashion, Jr.
Assistant Examiner—P. L. Prater
Attorney, Agent, or Firm—Cushman, Darby & Cushman

[57] ABSTRACT

An aromatic polycyclic compound has the formula

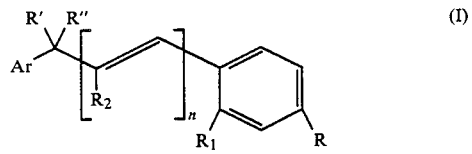
(I)

wherein
R represents —SO$_3$H, SO$_2$NHR$_3$,

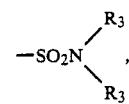

—SO$_2$R$_3$, —SOR$_3$ or —SR$_3$,

R$_3$ represents lower alkyl, monohydroxyalkyl, polyhydroxyalkyl, aminoalkyl, carboxyalkyl, aminocarboxyalkyl or alkoxyalkyl, R' represents hydrogen, lower alkyl, lower alkoxy, hydroxy, C$_1$–C$_4$ acyloxy or amino, R" represents hydrogen, lower alkyl or lower alkoxy, or R' and R", taken together, form an oxo, methano or hydroxyimino radical, R$_1$ represents hydrogen or lower alkyl, n is 0 or 1, when n=1, R$_2$ represents hydrogen or lower alkyl, or R$_1$ and R$_2$, taken together form a vinylene radical, and Ar represents an aromatic radical selected from

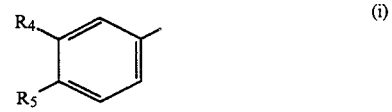
(i)

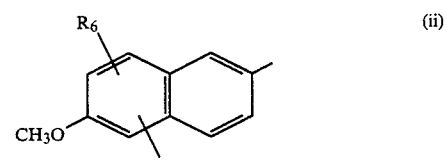

(ii)

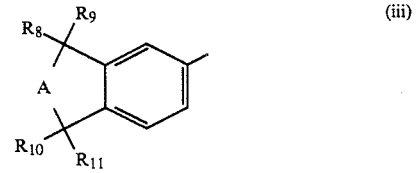

(iii)

wherein
R$_4$, R$_5$, R$_6$, R$_7$, R$_8$, R$_9$, R$_{10}$ and R$_{11}$ represent hydrogen or lower alkyl, at least one of R$_4$ and/or R$_5$ being other than hydrogen, and at least two of R$_8$–R$_{11}$ being other than hydrogen, A represents methylene or dimethylene substituted or not by lower alkyl; when A represents dimethylene, R$_8$ and R$_{10}$ together can form a methylene or dimethylene radical, and the salts of the compound of formula I as well as their geometric and optical isomers.

These compounds are useful in human and veterinary medicines and in cosmetic compositions.

3 Claims, No Drawings

NEW AROMATIC POLYCYCLIC DERIVATIVES, THEIR PROCESS OF PREPARATION AND THEIR USE IN HUMAN AND VETERINARY MEDICINE AND IN COSMETICS

The present invention relates to new aromatic polycyclic derivatives, their process of preparation and their use in human and veterinary medicine and in cosmetics.

The compounds according to the present invention are useful in the topical and systemic treatment of dermatologic diseases linked to a keratinization disorder (differentiation-proliferation) and dermatologic diseases (or others) having an inflammatory and/or immunoallergic component and in the treatment of illnesses of the degeneration of conjunctinve tissue, as well as an antitumoral activity.

Moreover, these compounds can be employed in the treatment of atophy, be it cutaneous or respiratory, and in the treatment of rheumatoid psoriasis.

The compounds are also usefully employed also find use in the ophtalmology field, and principally in the treatment of corneopathies.

The aromatic polycyclic compounds of the present invention can be represented by the following formula:

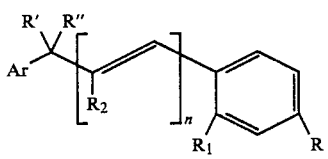

wherein
R represents —$SO_3H$, $SO_2NHR_3$,

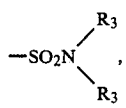

—$SO_2R_3$, —$SOR_3$ or —$SR_3$, $R_3$ represents linear or branched lower alkyl, monohydroxyalkyl, polyhydroxyalkyl, aminoalkyl, carboxyalkyl, aminocarboxyalkyl or alkoxyalkyl, R' represents hydrogen, lower alkyl, lower alkoxy, hydroxy, $C_1$-$C_4$ acyloxy or amino, R" represents hydrogen, lower alkyl or lower alkoxy, or R' and R", taken together, form an oxo radical (=O), a methano radical (=$CH_2$), or a hydroxyimino radical (=N—OH), $R_1$ represents hydrogen or lower alkyl, n is 0 or 1, when n=1, $R_2$ represents hydrogen or lower alkyl, or $R_1$ and $R_2$, taken together form a vinylene radical (—CH=CH—), and Ar represents an aromatic radical selected from

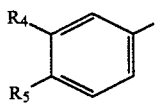

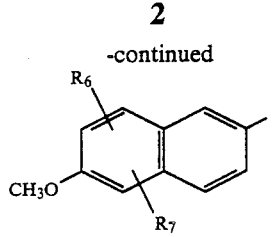

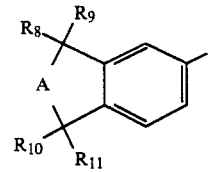

wherein
$R_4$, $R_5$, $R_6$, $R_7$, $R_8$, $R_9$, $R_{10}$ and $R_{11}$ represent hydrogen or lower alkyl, at least one of $R_4$ and/or $R_5$ being other than hydrogen, and at least two of $R_8$-$R_{11}$ being other than hydrogen, A represents methylene or dimethylene substituted or not by lower alkyl; when A represents dimethylene, $R_8$ and $R_{10}$ together can form a methylene or dimethylene radical, and the salts of said compounds of formula I as well as their geometric and optical isomers.

By linear or branched lower alkyl is meant a radical having 1 to 6 carbon atoms, in particular methyl, ethyl, isopropyl, butyl and tert. butyl.

By monohydroxy alkyl is meant a radical having 2 to 6 carbon atoms, principally 2-hydroxy ethyl or 2-hydroxypropyl.

By polyhydroxyalkyl is meant a radical having 3 to 6 carbon atoms and 2 to 5 hydroxyl groups such as 2,3-dihydroxy propyl, 1,3-dihydroxy propyl or the residue of pentaerythritol.

By aminoalkyl is meant a radical having 2 to 6 carbon atoms such as 2-amino ethyl, 2-aminopropyl or 3-aminopropyl.

By carboxyalkyl is meant a radical having 2 to 7 carbon atoms, such as carboxy methyl, 2-carboxyethyl, 2-carboxypropyl or 3-carboxybutyl.

By aminocarboxyalkyl is meant, preferably, 2-amino-2-carboxyethyl or 3-amino-3-carboxy propyl.

By lower alkoxy is meant a radical having 1 to 6 carbon atoms such as methoxy, ethoxy, butoxy or isopropoxy.

When the compounds according to the present invention are provided in the form of salts, it can be a question of salts of an alkali or alkaline earth metal or even of zinc or of an organic amine when they carry at least one free acid function, or of salts of a mineral or organic acid, principally hydrochloride, hydrobromide, or citrate when they carry at least one amine function.

Among the particularly preferred compounds of the present invention one can cite in particular those having the following formula:

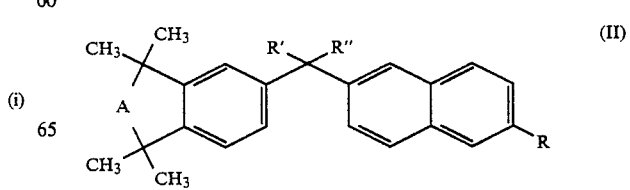

wherein

R represents —SO$_2$R'$_3$, SO$_2$NHR'$_3$, SOR'$_3$ or —SR'$_3$,

R'$_3$ represents lower alkyl,

R' represents hydrogen, hydroxyl or lower alkyl,

R" represents hydrogen, or R' and R" taken together form an oxo radical (=O) and A represents dimethylene or

Among the preferred compounds of formula I according to the invention one can principally mention:

methyl 4-[(5,6,7,8-tetrahydro-5,5,8,8-tetramethyl-2-naphthyl) hydroxymethyl]phenylsulfone, methyl 4-[(5,6,7,8-tetrahydro-5,5,8,8-tetramethyl-2-naphthyl)carbonyl] phenylsulfone, N-ethyl 4-[(5,6,7,8-tetrahydro-5,5,8,8-tetramethyl-2-naphthyl) hydroxymethyl] phenylsulfone, N-ethyl 4-[(5,6,7,8-tetrahydro-5,5,8,8-tetramethyl-2-naphthyl) carbonyl] phenylsulfonamide, methyl 4-[E3-(5,6,7,8-tetrahydro-5,6,7,8-tetramethyl-2-naphthyl)-3-oxo propenyl] phenylsulfone, methyl 4-[E3-(5,6,7,8-tetrahydro-5,5,8,8-tetramethyl-2-naphthyl)-3-oxo propenyl] phenylthioether, methyl 4-[E3-(5,6,7,8-tetrahydro-5,5,8,8-tetramethyl-2-naphthyl)-3-oxo propenyl] phenylsulfoxide, N-ethyl 4-[E3-(5,6,7,8-tetrahydro-5,5,8,8-tetramethyl-2-naphthyl)-3-oxo propenyl] phenylsulfonamide, methyl 4-[E3-(1,1,2,3,3-pentamethyl-5-indanyl)-3-oxo propenyl] phenylthioether, methyl 4-[E3-(1,1,2,3,3-pentamethyl-5-indanyl)-3-oxo propenyl] phenylsulfoxide, methyl 4-[E3-(1,1,2,3,3-pentamethyl-5-indanyl)-3-oxo propenyl] phenylsulfone, methyl 4-[E3-(1,1,2,3,3-pentamethyl-5-indanyl)-3-hydroxy propenyl] phenylsulfone, methyl 4-[E3-(5,6,7,8-tetrahydro-5,5,8,8-tetramethyl-2-naphthyl)-3-methoxy propenyl]phenylsulfone, ethyl 6-[(5,6,7,8-tetrahydro-5,5,8,8-tetramethyl-2-naphthyl) carbonyl] 2-naphthylsulfone, ethyl 6-[(1,1,2,3,3-pentamethyl-5-indanyl) carbonyl]-2-naphthylsulfone, ethyl 4-[E3-(1,1,3,3-tetramethyl-5-indanyl)-3-oxo propenyl] phenylsulfone, methyl 4-[E3-(1,1,2,3,3-pentamethyl-5-indanyl)-3-methoxy propenyl] phenylsulfone, ethyl 6-[(1,1,3,3-tetramethyl-5-indanyl) carbonyl]-2-naphthylsulfone, 2',3'-dihydroxypropyl 6-[(5,6,7,8-tetrahydro-5,5,8,8-tetramethyl-2-naphthyl) carbonyl]-2-naphthylsulfone, ethyl 6-[(5,6,7,8-tetrahydro-5,5,8,8-tetramethyl-2-naphthyl)hydroxymethyl]-2-naphthylsulfone, ethyl 6-[(5,8-methano-5,6,7,8-tetrahydro-2-naphthyl) carbonyl]-2-naphthylsulfoxide, ethyl-6-[(5,8-methano-5,6,7,8-tetrahydro-2-naphthyl) carbonyl]-2-naphthylsulfone, ethyl 6-[(5,6,7,8-tetrahydro-5,5,8,8-tetramethyl-2-naphthyl) methylene]-2-naphthylsulfone, ethyl 6-[1-(5,6,7,8-tetrahydro-5,5,8,8-tetramethyl-2-naphthyl)-1-hydroxy ethyl]-2-naphthylsulfone, N-ethyl 4-[(5,6,7,8-tetrahydro-5,5,8,8-tetramethyl-2-naphthyl)carbonyl]-2-naphthylsulfonamide, ethyl 6-[1-(5,6,7,8-tetrahydro-5,5,8,8-tetramethyl-2-naphthyl)-1-hydroxyethyl]-2-naphthylthioether, ethyl 6-[1-(5,6,7,8-tetrahydro-5,5,8,8-tetramethyl-2-naphthyl) ethenyl]-2-naphthylthioether, ethyl 6-[(5,6,7,8-tetrahydro-5,5,8,8-tetramethyl-2-naphthyl) carbonyl]-2-naphthylsulfoxide, ethyl 6-[(5,8-dimethyl-6-methoxy-2-naphthyl) carbonyl]-2-naphthylsulfone, ethyl 6-[(5,8-dimethyl-6-methoxy-2-naphthyl) hydroxymethyl]-2-naphthylsulfone, and ethyl 6[(5,8-dimethyl-6-methoxy-2-naphthyl) methylene]-2-naphthylsulfone.

The present invention also relates to the process for preparing the compounds of formula I.

These compounds can be obtained in accordance with various methods as a function of their structure.

In accordance with a first embodiment, the compounds of the present invention are obtained according to the following reaction scheme:

Scheme A

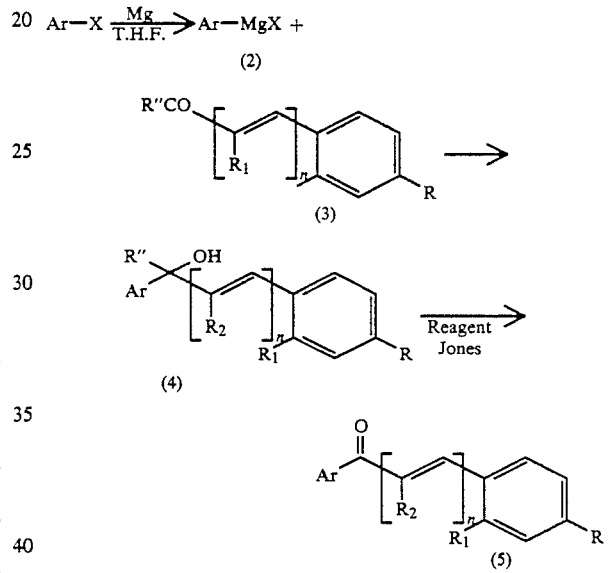

X=Br or Cl

R"=H or alkyl

This process comprises preparing in a first stage, an organomagnesium derivative (2) starting with an aromatic halogen compound (1) in accordance with a conventional method for preparing Grignard reagents.

This is then followed by reaction with an aldehyde of formula (3) (R"=H) or a ketone of formula (3) (R"=lower alkyl) in an organic solvent such as tetrahydrofuran (T.H.F.) at a temperature between −10° C. and +20° C., but preferably about 0° C.

When the compound of formula (3) is an aldehyde, the resulting secondary alcohol (4) (R"=H) can be oxidized to the corresponding carbonyl compound (5) using as an oxidizing agent a Jones reagent.

The aromatic halogen compounds (1) are preferably bromo derivatives such as:

2-bromo-5,6,7,8-tetrahydro-5,5,8,8-tetramethyl naphthalene, 5-bromo-1,1,3,3-tetramethyl indane, 5-bromo-1,1,2,3,3-pentamethyl indane, 2-bromo-5,8-methano-5,6,7,8-tetrahydro naphthalene, and 2-bromo-5,8-dimethyl-6-methoxy naphthalene.

These bromo derivatives are obtained by the action of bromine on respectively:

1,2,3,4-tetrahydro-1,1,4,4-tetramethyl naphthalene, prepared in accordance with the method described in J. Am. Chem. Soc., 63, 36–44, (1940), 1,1,3,3-tetramethyl indane and 1,1,2,3,3-pentamethyl indane prepared in accordance with the operating procedure described in French patent No. 1.392.804, 1,4-methano-1,2,3,4-tetrahydro naphthalene or benzonorbornene prepared in accordance with the method described in J. Org. Chem., 32, 893–901, (1967), and 5,8-dimethyl-6-methoxy naphthalene prepared in accordance with the method described by M. Fetizon and N.T. Anh, Bull. Soc. Chim. Fr., 3028, (1965).

The aldehydes or ketone of formula (3) are commercial products or can be obtained according to conventional methods.

When in the compounds of formula I, n=0 or n=1 and $R_1$ and $R_2$, taken together, form a vinylidene radical (naphthalenic ring), they are preferably obtained in accordance with the following reaction scheme:

Scheme B

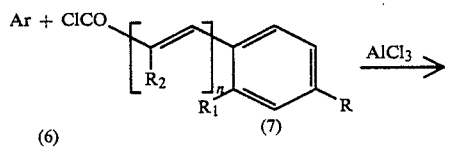

(6)        (7)

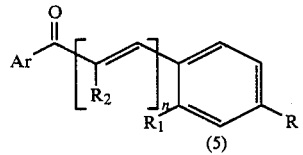

(5)

This method comprises acylating, under conventional Friedel-Crafts reaction conditions, an aromatic compound (6) by a benzene or naphthalene acid chloride of formula (7). The acid chlorides of formula (7) are easily obtained starting with benzene or naphthalene thioethers.

When in the compounds of formula I, n=1 and $R_1$ and $R_2$ represent hydrogen or lower alkyl radical, they are obtained preferably in accordance with the following reaction scheme:

Scheme C

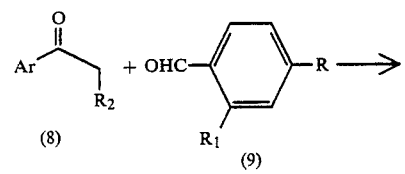

(8)        (9)

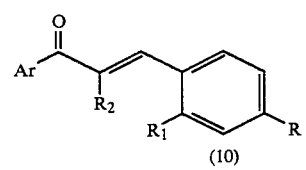

(10)

This method comprises condensing, under the Claisen-Schmidt reaction conditions, a benzene aldehyde (9) with an aromatic ketone of formula (8). Preferably, the reaction is carried out in the presence of soda or potash in an organic solvent such as ethanol. This process produces unsaturated ketones of "E" configuration in good yields. The nature of the radical R must be compatible with this type of condensation, it being suitable when R is a thioether, sulfoxide, sulfone or sulfonamide radical.

Starting with carbonyl compounds (5) and (10), other compounds of the present invention can be produced.

Thus, the compounds in which R'=OH and R''=H are obtained by reduction in the presence of sodium borohydride in an organic solvent such as ethanol or T.H.F.

The compounds in which R'=R''=H are obtained by reduction with zinc of the ketone derivatives (R' and R''=oxo) in acetic acid in the presence of HCl.

These reduction reactions must, however, be compatible with the nature of the radical R but they raise no difficulty when R=$SO_2R_3$.

The compounds in which R'=acyloxy and R''=H are obtained by reacting an acid active form, such as an anhydride or chloride of the acid with a compound of formula I in which R'=OH and R''=H.

The compounds in which R'=alkoxy and R''=H are also obtained starting with compounds of formula I in which R'=OH and R''=H in accordance with known methods.

The compounds of formula I in which R' and R''=methano (=$CH_2$) are obtained by the Witting reaction in accordance with the following reaction scheme:

Scheme D

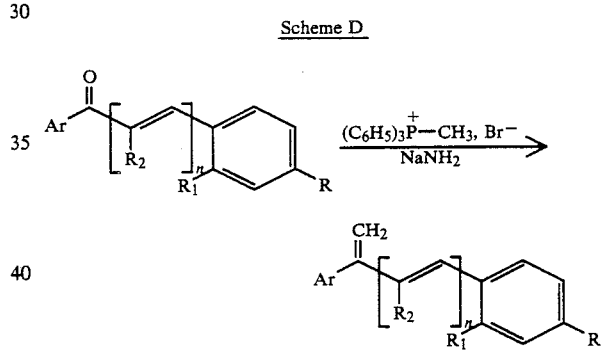

The compounds of formula I wherein R' and R''=hydroxyimino (=N—OH) are obtained by the action of hydroxylamine on corresponding carbonyl compounds.

The present invention also relates to a medicine comprising the compounds of formula I as defined above.

The compounds, due to the fact of the presence of a substitution by a thioether function or oxidation derivatives, are less toxic than corresponding derivatives substituted by a carboxylic function.

These compounds are particularly suitable for treating dermatologic ailments linked to a keratinization disorder (differentiation-proliferation) as well as dermatologic diseases, or others, having an inflammatory and/or immunoallergic component, principally:

acne vulgaris, comedons or polymorphs, solar senile acne, and medicinal or professional acne, extensive and/or severe forms of psoriasis and other keratinization disorders, and principally ichtysoses and ichtysosis-like conditions, Darier malady, palmo-plantar keratodermies, leucophasies and leucophasie-like states, lichen plan, all malignant or benign dermatologic proliferations, severe or extensive.

They are also active in the treatment of tumors, of rheumatoid psoriasis, cutaneous or respiratory atrophies as well as in certain opthalmologic problems relating to corneopathies.

Thus, the present invention also relates to medicinal compositions containing at least one compound of formula I, such as defined above, or one of its salts or one of its isomers.

The present invention thus relates to a new medicinal composition, intended principally for the treatment of the above-mentioned disorders, comprising in a pharmaceutically acceptable support, an effective amount of at least one compound of formula I and/or one of its salts and/or one of its isomers.

The compounds according to the present invention are generally administered at a daily dosage of about 0.01 mg/kg to 5 mg/kg of body weight.

As the vehicle or carrier for these compositions any conventional vehicle can be employed, the active component being found either in the dissolved state, or in the dispersed state, in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds according to the present invention, can be provided in the form of ointments, tinctures, creams, salves, powders, pads, impregnated tampons, solutions, lotions, gels, sprays or suspensions.

These compositions for topical administration can be provided under anhydrous form or in aqueous form according to clinical indications.

When administered ocularly, the composition is provided principally in the form of an eyewash.

The compositions for topical or ocular administration contain from 0.0001 to about 5 percent of at least one compound of formula I such as defined above and preferably from 0.001 to 1 percent by weight relative to the total weight of the composition.

The compounds of formula I, according to the present invention, are also useful in the cosmetic field, in particular in body and hair hygiene compositions and principally for the treatment of skin having acne tendencies, to improve the growth of hair, to combat hair loss, to combat against an oily appearance of the skin or hair, in the prevention or treatment of the harmful effects of the sun or in the treatment of physiologically dry skin.

The present invention thus relates to a cosmetic composition containing, in a cosmetically acceptable vehicle, an effective amount of at least one compound of formula I or one of its salts and/or one of its isomers, this composition being provided principally in the form of a lotion, gel, soap, shampoo or cream.

The concentration of the compound of formula I in these cosmetic compositions is between 0.0001 and 2 percent by weight and, preferably, between 0.001 and 1 percent by weight based on the total weight of the composition.

The medicinal and cosmetic compositions according to the present invention can contain inert or even pharmacodynamic or cosmetically active additives and, principally: hydrating agents such as thiamorpholinone and its derivatives or urea; antiseborrheic or anti-acne agents such as S-carboxymethylcysteine, S-benzylcysteamine, their salts and their derivatives, tioxolone or benzoyl peroxide; antibiotics such as erythromycin and its esters, neomycin, tetracyclines and 4,5-polymethylene-3-isothiazolones; agents promoting the growth of hair such as "Minoxidil" (2,4-diamino-6-piperidino-3-pyrimidine oxide) and its derivatives, Diazoxide (7-chloro-3-methyl-1,2,4-benzothiadiazine-1,1-dioxide) and Phenytoin (5,5-diphenyl-2,4-imidazolidinedione; steroidal and nonsteroidal anti-inflammatory agents; carotenoids and, principally, $\beta$-carotene; anti-psoriasic agents such as anthralin and its derivatives and 5,8,11,14-eicosatetraynoic and 5,8-11-eicosatriynoic acids and their esters and amides.

The compositions according to the present invention can also include flavor improving agents, preservatives, stabilizers, humidity regulating agents, pH regulating agents, emulsifiers, UV-A and UV-B filters, antioxidants such as $\alpha$-tocopherol, butylhydroxy anisole or butylhydroxy toluene.

The following nonlimiting examples illustrate the preparation of the active compounds of formula I according to the present invention, as well as compositions containing these compounds.

Examples A to E concern the preparation of synthesis intermediates to obtain the compounds of general formula I.

All structures described in these various examples are confirmed by NMR$^1$H 80 MHz and in a certain case by NMR$^{13}$C 100 MHz.

In the examples of preparing the compounds, the progress of the reaction media is always followed by thin layer chromatography (TLC). The indicated reaction times correspond then to the majority of the initial reactant being transformed.

EXAMPLE A

Preparation of 4-methylsulfonyl benzaldehyde and of 4-methylsulfinyl benzaldehyde To a stirred solution of 30 g of 4-methylthio benzaldehyde in 250 cm$^3$ of formic acid, there are slowly added at ambient temperature 44 cm$^3$ of H$_2$O$_2$ 30% (2 equivalents). The reaction is exothermic and the temperature rises up to 75° C. When the starting product is completely transformed, the resulting solution is concentrated to about 50 cm$^3$ and then poured into water. The mixture is then neutralized by the addition of 6N soda, extracted three times with 200 cm$^3$ of ethyl acetate and the combined organic phases are washed with an aqueous solution of sodium hydrosulfite, then with water and finally dried on magnesium sulfate. The solvent is removed by evaporation under a vacuum. The resulting solid is dissolved in toluene and the solution is deposited on a silica gel chromatography column. By using as eluant a 7/3 ethyl acetate/heptane mixture, then after evaporation of the eluant phase, 16 g of 4-methylsulfonyl benzaldehyde and 7 g of 4-methylsulfinyl benzaldehyde are isolated.

EXAMPLE B

Preparation of 4-N-ethyl formyl phenylsulfonamide

A suspension of 26 g of paratoluene sulfochloride in 200 cm³ of water is cooled to 0° C. With stirring there are slowly added 100 cm³ of a 40% aqueous solution of ethylamine in water. At the end of the addition the reaction mixture is again stirred for two hours at 0° C., then for two hours at ambient temperature. The solid in suspension is filtered, washed several times with water, then dried under reduced pressure. 24 g of N-ethyl(4-methyl phenyl) sulfonamide are obtained.

To a solution of 15 g of N-ethyl(4-methyl phenyl) sulfonamide in 75 cm³ of acetic anhydride there are slowly added, at ambient temperature, 18 cm³ of concentrated sulfuric acid.

To this solution, cooled to 0° C., there is very slowly added a solution of 21 g of chromium oxide dissolved in 90 cm³ of acetic anhydride. The addition complete, the mixture is maintained for one hour at 0° C., then it is left to stand overnight at ambient temperature. The next day, the mixture is poured into 1 liter of ice water and extracted three times with 200 cm³ of ethyl acetate. The combined organic phases are washed with an aqueous solution of sodium bicarbonate until the wash water has a pH of 6. The ethyl acetate solution is dried on magnesium sulfate and concentrated. The resulting viscous liquid is then stirred for 3 days at 50° C. in 1 liter of N HCl. This acid solution is then extracted three times with 150 cm³ of ethyl acetate. The ethyl acetate phases are washed with a saturated aqueous solution of ammonium chloride, then with water and finally dried on magnesium sulfate.

On evaporation under a vacuum of ethyl acetate, 7 g of N-ethyl (4-formyl phenyl) sulfonamide are obtained.

EXAMPLE C

Preparation of 2-acetyl-6-ethylthio naphthalene and its sulfone (1) 2-ethylthio naphthalene To a solution, stirred under an inert atmosphere at ambient temperature, of 40 g of 2-mercapto naphthalene in 1 liter of anhydrous ethanol, there are slowly added 24.4 g of potash. The addition being completed, stirring is maintained for 2 hours, then there is slowly added a solution of 21 cm³ of bromomethane dissolved in 100 cm³ of anhydrous ethanol. After 3 hours of stirring, the reaction mixture is left overnight, then filtered and the filtrate is concentrated under a vacuum. The resulting crude product is stirred in 800 cm³ of water, then extracted 4 times with 150 cm³ of dichloromethane. The dichloromethane phases are combined, washed with a saturated solution of ammonium chloride, then dried on magnesium sulfate. The solvent is rectified under vacuum and 38 g of 2-ethylthio naphthalene are obtained and used as such for the following reactions.

(2) 2-acetyl-6-ethylthio naphthalene

To a mixture, stirred in the absence of the humidity of the air, of 10 g of 2-ethylthio naphthalene and 4.5 cm³ of acetyl chloride in 200 cm³ of 1,2-dichloro ethane, there are added, in small portions, 11 g of aluminum chloride in a manner to maintain the temperature at 30° C.

At the end of the addition the reaction mixture is again stirred for 3 hours at ambient temperature, then poured into 200 cm³ of a saturated aqueous solution of ammonium chloride. The mixture is extracted three times with 100 cm³ of dichloromethane and the combined organic phases are washed with sodium bicarbonate, then dried on magnesium sulfate and concentrated.

7 g of 2-acetyl-6-ethylthio naphthalene whose melting point is 69° C. are obtained.

(3) 2-acetyl-6-ethylsulfonyl naphthalene

To a solution of 7 g of 2-acetyl-6-ethylthio naphthalene in 200 cm³ of dichloromethane, stirred at 0° C., there are added in small amounts, 14 g of metachloroperbenzoic acid. The addition complete, stirring of the reaction mixture is maintained for 3 hours at 0° C. and then for 2 hours at ambient temperature. The mixture is then poured into 300 cm³ of a saturated aqueous solution of ammonium chloride, and extracted three times with 100 cm³ dichloromethane. The combined organic phases are then washed with a dilute solution of sodium bicarbonate, dried on magnesium sulfate and concentrated. The resulting solid is then washed with a 10/5 heptane/toluene mixture heated to 50° C. After drying, 7 g of 2-acetyl-6-ethylsulfonyl naphthalene in the form of yellow crystals having a melting point of 133° C. are obtained.

EXAMPLE D

Preparation of 6-ethylsulfonyl-2-naphthalene carboxylic acid chloride (1) 6-ethylsulfonyl-2-naphthalene carboxylic acid There is prepared in a first stage a solution of sodium hypobromite by adding, at 0° C., 3 cm³ of bromine to a stirred solution containing 7.5 g of soda in 35 cm³ of water. Then, there is slowly introduced a suspension of 1 g of 2-acetyl-6-ethylsulfonyl naphthalene dispersed in 20 cm³ of dioxan in a fashion to maintain the temperature of the reaction mixture lower than 5° C. At the end of the addition, this temperature is again maintained for 1 hour and then there are slowly added at ambient temperature 15 g of sodium metabisulfite dissolved in 150 cm³ of water. On acidifying the mixture with HCl, the anticipated acid precipitates. It is filtered, washed thoroughly with water and dried. 0.95 g of 6-ethylsulfonyl-2-naphthalene carboxylic acid in the form of a white powder whose melting point is 241° C. is obtained.

(2) 6-ethylsulfonyl-2-naphthalene carboxylic acid chloride

A suspension of 1 g of the preceding acid in 30 cm³ of thionyl chloride is heated at 60° C. for 1 hour. The starting acid is progressively dissolved. The thionyl chloride is then removed by evaporation under a vacuum and the resulting solid is washed with hexane. 1 g of 6-ethylsulfonyl-2-naphthalene carboxylic acid chloride in the form of a brown powder which is directly used for the Friedel-Crafts reactions is obtained.

EXAMPLE E

Preparation of 5-acetyl-1,1,2,3,3-pentamethyl indane

To a mixture, stirred at ambient temperature in the absence of the humidity of the air, of 25 g of 1,1,2,3,3-pentamethyl indane and 13 cm³ of acetyl chloride, there are added, in small portions, 23 g of aluminum chloride in a manner such that the temperature does not exceed 40° C. Stirring is maintained for 2 hours after the end of the addition and the reaction mixture is left overnight. The next day, it is poured into 200 cm³ of ice water and then extracted three times with 150 cm³ of dichloromethane. The organic phases are combined, washed with sodium bicarbonate and then with water and dried on magnesium sulfate. The solvent is removed by evaporation under a vacuum and 31 g of 5-acetyl-1,1,2,3,3-pentamethyl indane in liquid form which is directly used for the following reactions are obtained.

EXAMPLE I

Preparation of methyl 4-[(5,6,7,8-tetrahydro-5,5,8,8-tetramethyl-2-naphthyl) hydroxymethyl] phenylsulfone To a solution, stirred in the absence of the humidity of the air, of 5 g of 2-bromo-5,6,7,8-tetrahydro-5,5,8,8-tetramethyl naphthalene in 30 cm$^3$ of anhydrous tetrahydrofuran, there is added all at once 0.5 g of magnesium. The reaction is primed by heating a very localized place of the reaction mixture when stirring is stopped. When the solvent reaches its boiling point, the mixture is diluted by the addition of 80 cm$^3$ of T.H.F., then, with stirring, the mixture is heated at reflux for one hour, at the end of which time, the magnesium is transformed. The resulting solution is then cooled to 0° C. and there is slowly added a solution of 1.72 g of 4-methylsulfonyl benzaldehyde, obtained in Example A above, in 80 cm$^3$ of THF. The reaction mixture is colored yellow. Stirring is again maintained for 1 hour at 0° C., and then the reaction mixture is left overnight at ambient temperature. The next day, it is poured into 200 cm$^3$ of a saturated solution of ammonium chloride. The resulting mixture is then extracted three times with 150 cm$^3$ of diethylether and the combined organic phases are washed with 200 cm$^3$ of water, then dried on magnesium sulfate and concentrated. 5 g of a yellow liquid that is crystallized in hexane at $-25°$ C. is obtained. The crystals are filtered and after drying, 3.5 g of crystals recrystallized in a toluene-hexane mixture are obtained.

2 g of methyl 4-[(5,6,7,8-tetrahydro-5,5,8,8-tetramethyl-2-naphthyl) hydroxymethyl] phenylsulfone provided in the form of white crystals whose melting point is 134° C. are obtained Elemental analysis: $C_{22}H_{28}O_3S$

|  | C | H | O | S |
|---|---|---|---|---|
| Calculated | 70.93 | 7.57 | 12.89 | 8.61 |
| Found | 71.03 | 7.63 | 13.01 | 8.30 |

EXAMPLE II

Preparation of methyl 4-[(5,6,7,8-tetrahydro-5,5,8,8-tetramethyl-2-naphthyl) carbonyl] phenylsulfone To a solution, stirred at ambient temperature, of 2.5 g of methyl 4-[(5,6,7,8-tetrahydro-5,5,8,8-tetramethyl-2-naphthyl) hydroxymethyl] phenylsulfone, obtained in Example I, in 100 cm$^3$ of acetone, there is slowly added the Jones reagent prepared previously by adding 1.9 cm$^3$ of concentrated sulfuric acid to a solution of 2.2 g of potassium bichromate dissolved in 15 cm$^3$ of water. At the end of the addition, the mixture is again stirred for two hours, then left overnight at ambient temperature.

The acetone is then removed by evaporation under a vacuum and the resulting mixture is taken up in 200 cm$^3$ of water and extracted three times with 100 cm$^3$ of diethylether. The combined organic phases are washed with an aqueous solution of sodium bicarbonate, then with water and finally dried on magnesium sulfate.

After evaporation of the solvent, 2 g of a white powder are obtained and dissolved in a minimum of toluene. The solution is deposited on a silica gel column and the expected product eluted with 4/2 hexane/ethyl acetate mixture. After evaporation of the eluant, 1.5 g of methyl 4-[(5,6,7,8-tetrahydro-5,5,8,8-tetramethyl-2-naphthyl) carbonyl] phenylsulfone in the form of a white powder whose melting point is 161° C. are obtained.

Elemental analysis: $C_{22}H_{26}O_3S$

|  | C | H | O | S |
|---|---|---|---|---|
| Calculated | 71.31 | 7.07 | 12.96 | 8.65 |
| Found | 70.91 | 7.19 | 13.24 | 8.55 |

EXAMPLE III

Preparation of N-ethyl 4-[(5,6,7,8-tetrahydro-5,5,8,8-tetramethyl-2-naphthyl) hydroxymethyl] phenylsulfone Following the procedures described in Example I, there is transformed into the corresponding organomagnesium, 2.5 g of 2-bromo-5,6,7,8-tetrahydro-5,5,8,8-tetramethyl naphthalene dissolved in 30 cm$^3$ of THF by the addition of 0.27 g of magnesium.

To this solution cooled to 0° C., there is slowly added a solution of 4-N-ethyl formyl phenyl sulfonamide (obtained in Example B) dissolved in 20 cm$^3$ of THF.

The mixture is stirred for 2 hours at ambient temperature then left overnight. It is then poured into 100 cm$^3$ of a saturated aqueous solution of ammonium chloride and then extracted three times with 100 cm$^3$ of diethylether.

The combined organic phases are washed with water, dried on magnesium sulfate and concentrated under reduced pressure. The crude product is dissolved in a minimum of toluene and deposited on a silica gel chromatography column. After elution with a 1/1 hexane/ethyl acetate mixture and concentration of the eluant, the expected product crystallizes in a hexane/isopropyl ether mixture. 0.8 g of N-ethyl 4-[(5,6,7,8-tetrahydro-5,5,8,8-tetramethyl-2-naphthyl) hydroxy methyl] phenyl sulfonamide in the form of white crystals whose melting point is 175° C. is obtained.

Elemental analysis: $C_{23}H_{31}NO_3S$

|  | C | H | N | O | S |
|---|---|---|---|---|---|
| Calculated | 68.79 | 7.78 | 3.49 | 11.95 | 7.99 |
| Found | 68.76 | 7.76 | 3.35 | 11.87 | 7.94 |

In the course of this reaction, the secondary alcohol obtained is partially oxidized into the corresponding carbonyl derivative described in Example IV.

EXAMPLE IV

Preparation of N-ethyl 4-[(5,6,7,8-tetrahydro-5,5,8,8-tetramethyl-2-naphthyl)-carbonyl] phenylsulfonamide To a solution, stirred at ambient temperature, of 2 g of N-ethyl 4-[(5,6,7,8-tetrahydro-5,5,8,8-tetramethyl-2-naphthyl) hydroxymethyl] phenyl sulfonamide, prepared in Example III, in 100 cm$^3$ of acetone, there is added the Jones reagent prepared in accordance with Example II. The reaction mixture is then treated under the same conditions. The carbonyl derivative is purified by passage through a silica gel chromatography column. It is eluted with a 4/1 hexane/ethyl acetate mixture and recrystallized in a hexane/isopropyl ether mixture. 1.5 g of N-ethyl 4-[(5,6,7,8-tetrahydro-5,5,8,8-tetramethyl-2-naphthyl) carbonyl]phenylsulfonamide are obtained.

It is a white solid whose melting point is 134° C.

Elemental analysis: $C_{23}H_{29}NO_3S$

|  | C | H | N | O | S |
|---|---|---|---|---|---|
| Calculated | 69.14 | 7.32 | 3.51 | 12.01 | 8.03 |
| Found | 69.28 | 7.34 | 3.42 | 12.05 | 7.94 |

EXAMPLE V

Preparation of methyl 4-[E3-(5,6,7,8-tetrahydro-5,5,8,8-tetramethyl-2-naphthyl)-3-oxo propenyl] phenylsulfone To a solution of 2.3 g of potash in a mixture of 80 cm³ of water and 30 cm³ of ethanol, stirred in the absence of light and at ambient temperature, there is rapidly added a suspension containing 4.6 g of 2-acetyl-5,6,7,8-tetrahydro-5,5,8,8-tetramethyl naphthalene and 3.7 g of 4-methyl formyl phenylsulfone in 70 cm³ of ethanol.

Stirring is maintained for 3 hours and the reaction mixture is left for 2 days at ambient temperature, at the end of which time the 4-formyl phenylsulfone is completely transformed. The ethanol is then removed by evaporation under a vacuum and the resulting suspension is taken up in 200 cm³ of water, then extracted three times with 150 cm³ of ethyl acetate. The ethyl acetate phases are combined, washed with a saturated aqueous solution of ammonium chloride, then with water and dried on magnesium sulfate.

After evaporation, under reduced pressure, of the ethyl acetate, 6.5 g of the resulting yellow powder are recrystallized in a toluene/hexane mixture. 3.5 g of methyl 4-[E3-(5,6,7,8-tetrahydro-5,6,7,8-tetramethyl-2-naphthyl)-3-oxo propenyl]phenylsulfone in the form of light yellow crystals whose melting point is 135° C. are obtained.

Elemental analysis: $C_{24}H_{28}O_3S$

|  | C | H | O | S |
|---|---|---|---|---|
| Calculated | 72.69 | 7.12 | 12.10 | 8.09 |
| Found | 72.87 | 7.07 | 12.39 | 7.90 |

EXAMPLE VI

Preparation of methyl 4-[E3-(5,6,7,8-tetrahydro-5,5,8,8-tetramethyl-2-naphthyl)-3-oxo propenyl] phenylthioether There is added in the absence of light and at ambient temperature a solution of 6.5 g of 3-methylthio benzaldehyde and 10 g of 2-acetyl-5,6,7,8-tetrahydro-5,5,8,8-tetramethyl naphthalene in 140 cm³ of ethanol to a stirred solution of 5.8 g of potash dissolved in a mixture of 160 cm³ of water and 60 cm³ of ethanol. Stirring is again maintained for 4 hours at ambient temperature and then the reaction mixture is left overnight. The next day the ethanol is removed by evaporation under a vacuum and the resulting suspension is taken up in 200 cm³ of water, then extracted three times with 200 cm³ of ethyl acetate. The combined ethyl acetate phases are washed with a saturated aqueous solution of ammonium chloride and dried on magnesium sulfate. The ethyl acetate is removed by evaporation under a vacuum and the resulting 16 g of yellow product are purified by silica gel chromatogrpahy. The expected product is eluted with a 9.5/0.5 hexane/ethyl acetate mixture. After evaporation of the eluant and recrystallization in hexane containing traces of toluene, 7.2 g of methyl 4-[E3-(5,6,7,8-tetrahydro-5,5,8,8-tetramethyl-2-naphthyl)-3-oxo propenyl] phenylthioether in the form of a yellow powder whose melting point is 124° C. are obtained.

Elemental analysis: $C_{24}H_{28}OS$

|  | C | H | S |
|---|---|---|---|
| Calculated | 79.07 | 7.74 | 8.80 |
| Found | 78.95 | 7.74 | 8.53 |

EXAMPLE VII

Preparation of methyl 4-[E3-(5,6,7,8-tetrahydro-5,5,8,8-tetramethyl-2-naphthyl)-3-oxo propenyl] phenylsulfoxide To a solution, stirred at 0° C. in the absence of light, of 2 g of methyl 4-[E3-(5,6,7,8-tetrahydro-5,5,8,8-tetramethyl-2-naphthyl)-3-oxo propenyl] phenylthioether, obtained in Example VI, in 100 cm³ of dichloromethane there is added in small amounts, one equivalent of metalchloroperbenzoic acid. The transformation of the thioether into sulfoxide is followed by thin layer chromatography (TLC). When it is complete, the reaction mixture is poured into a saturated aqueous solution of ammonium chloride, then extracted three times with 100 cm³ of dichloromethane. The organic phases are combined, washed with an aqueous solution of sodium bicarbonate, dried on magnesium sulfate, concentrated and then deposited on a silica gel chromatography column. The expected sulfoxide is eluted with ethyl acetate.

After concentration of the eluant and recrystallization in hexane, 1.4 g of methyl 4-[E3-(5,6,7,8-tetrahydro-5,5,8,8-tetramethyl-2-naphthyl)-3-oxo propenyl] phenylsulfoxide in the form of white crystals whose melting point is 116° C. are obtained.

Elemental analysis: $C_{24}H_{28}O_2S$

|  | C | H | O | S |
|---|---|---|---|---|
| Calculated | 75.75 | 7.41 | 8.41 | 8.43 |
| Found | 75.45 | 7.44 | 8.88 | 8.02 |

EXAMPLE VIII

Preparation of N-ethyl 4-[E3-(5,6,7,8-tetrahydro-5,5,8,8-tetramethyl-2-naphthyl)-3-oxo propenyl] phenylsulfonamide To a solution, stirred at ambient temperature in the absence of light, of 0.6 g of potash in 20 cm³ of water and 10 cm³ of ethanol, there is rapidly added a mixture of 1.05 g of 2-acetyl-5,6,7,8-tetrahydro-5,5,8,8-tetramethyl naphthalene and 0.95 g of 4-N-ethylformyl phenyl sulfonamide dissolved in 20 cm³ of ethanol. The addition completed, stirring is again maintained for 4 hours and the reaction mixture is left overnight. The ethanol is evaporated under reduced pressure and the resulting product is stirred in 200 cm$^3$ of water, then extracted three times with 150 cm$^3$ of ethyl acetate. The combined organic phases are washed with a saturated aqueous solution of ammonium chloride and dried on magnesium sulfate. The ethyl acetate is removed by evaporation under a vacuum and 1.3 g of solid that one recrystallizes in a 1/1 toluene/hexane mixture are obtained.

The N-ethyl 4-[E3-(5,6,7,8-tetrahydro-5,5,8,8-tetramethyl-2-naphthyl)-3-oxo propenyl] phenylsulfonamide is a white solid whose melting point is 147° C.

Elemental analysis: $C_{25}H_{31}NO_3S$

|  | H | N | O | S |
|---|---|---|---|---|
| Calculated | 70.55 | 7.34 | 3.29 | 11.28 | 7.53 |
| Found | 70.59 | 7.35 | 3.25 | 11.06 | 7.48 |

EXAMPLE IX

Preparation of methyl 4-[E3-(1,1,2,3,3-pentamethyl-5-indanyl)-3-oxo propenyl] phenylthioether In the same manner as set forth in Example VI a mixture of 10 g f 5-acetyl-1,1,2,3,3-pentamethyl indane and 6.5 g of 4-methylthiobenzaldehyde dissolved in 140 cm$^3$ of ethanol are added in the absence of light to a solution of 5.8 g of potash in ethanol. At the end of the reaction, the reaction mixture is treated in the manner set forth in Example VI.

The expected thioether is purified by passage through a silica gel column, using as the eluant a 9/1 hexane/ethyl acetate mixture. After evaporation of the eluant, the remainder is recrystallized in a hexane/toluene mixture. 5 g of methyl 4-[E3-(1,1,2,3,3-pentamethyl-5-indanyl)-3-oxo propenyl] phenyl thioether in the form of light yellow crystals whose melting point is 109° C. are obtained.

Elemental analysis: $C_{24}H_{28}OS$

|  | C | H | S |
|---|---|---|---|
| Calculated | 79.07 | 7.74 | 8.80 |
| Found | 78.72 | 7.74 | 8.52 |

EXAMPLE X

Preparation of methyl 4-[E3-(1,1,2,3,3-pentamethyl-5-indanyl)-3-oxo propenyl] phenylsulfoxide To a solution, stirred at 0° C. in the absence of light, of 2.3 g of methyl 4-[E3-(1,1,2,3,3-pentamethyl-5-indanyl)-3-oxo propenyl] phenyl thioether, prepared in accordance with Example IX, in 100 cm$^3$ of dichloromethane, there are added, in small amounts, one equivalent of metachloroperbenzoic acid. After the end of the addition, the reaction mixture is again stirred for two hours at 0° C., then for one hour at ambient temperature at the end of which time all of the thioether is transformed. The mixture is then poured into 200 cm$^3$ of an aqueous solution of ammonium chloride and extracted three times with 100 cm$^3$ of dichloromethane and the combined organic phases are washed with an aqueous solution of sodium bicarbonate, then dried on magnesium sulfate and finally concentrated.

The crude product is purified by silica gel chromatography using as the eluant ethylacetate. After evaporation of the eluant, the residue is recrystallized in cyclohexane and 0.9 g of methyl 4-[E3-(1,1,2,2,3,3-pentamethyl-5-indanyl)-3-oxo propenyl] phenylsulfoxide in the form of white crystals whose melting point is 113° C. is obtained.

Elemental analysis: $C_{24}H_{28}O_2S$

|  | C | H | O | S |
|---|---|---|---|---|
| Calculated | 75.75 | 7.41 | 8.41 | 8.43 |
| Found | 75.64 | 7.40 | 8.50 | 8.26 |

EXAMPLE XI

Preparation of methyl 4-[E3-(1,1,2,3,3-pentamethyl-5-indanyl)-3-oxo propenyl] phenylsulfone To a solution of 2.3 g of potash in a mixture of 30 cm$^3$ of ethanol and 80 cm$^3$ of water, stirred in the absence of light at ambient temperature, there is rapidly added a mixture of 4.6 g of 2-acetyl-1,1,2,3,3-pentamethyl indane and 3.7 g of 4-methylsulfonyl benzaldehyde in 70 cm$^3$ of ethanol. After 4 hours of stirring at ambient temperature, the reaction is terminated.

The ethanol is evaporated under reduced pressure and the resulting suspension is taken up in 200 cm$^3$ of water, then extracted three times with 150 cm$^3$ of ethyl acetate. The ethyl acetate phases are combined, washed with a saturated aqueous solution of ammonium chloride, dried on magnesium sulfate and concentrated. The resulting solid is recrystallized twice in hexane in the presence of a trace of toluene. 2.1 g of methyl 4-[E3-(1,1,2,3,3-pentamethyl-5-indanyl)-3-oxo propenyl] phenylsulfone in the form of white crystals whose melting point is 119° C. are obtained.

Elemental analysis: $C_{24}H_{28}O_3S$

|  | C | H | O | S |
|---|---|---|---|---|
| Calculated | 72.69 | 7.12 | 12.10 | 8.09 |
| Found | 72.28 | 7.13 | 12.34 | 7.88 |

EXAMPLE XII

Preparation of methyl 4-[E3-(1,1,2,3,3-pentamethyl-5-indanyl)-3-hydroxy propenyl] phenylsulfone To a suspension of 1 g of methyl 4-[E3-(1,1,2,3,3-pentamethyl-5-indanyl)-3-oxo propenyl] phenylsulfone, obtained in Example XI, in 80 cm$^3$ of methanol, stirred in the absence of light at 0° C., there is added all at once, 0.1 g of sodium borohydride.

Stirring is maintained for 4 hours at this temperature, then the reaction mixture is left to stand for 48 hours at ambient temperature. The methanol is then removed by evaporation under a vacuum and the crude product is taken up in 200 cm$^3$ of water. It is extracted three times with 100 cm$^3$ of ethyl acetate and the ethyl acetate phases are combined, washed with a saturated aqueous solution of ammonium chloride, dried on magnesium sulfate and concentrated under reduced pressure. The crude product is deposited on a silica gel chromatography column using as the eluant ethyl acetate. After concentration 0.5 g of methyl 4-[E3(1,1,2,3,3-pentamethyl-5-indanyl)-3-hydroxy propenyl] phenylsulfone in the form of a white powder whose melting point is 68° C. is obtained.

Elemental analysis: $C_{24}H_{30}O_3S$

|  | C | H | O | S |
|---|---|---|---|---|
| Calculated | 72.32 | 7.59 | 12.04 | 8.05 |
| Found | 72.17 | 7.79 | 11.97 | 7.75 |

EXAMPLE XIII

Preparation of methyl 4-[E3-(5,6,7,8-tetrahydro-5,5,8,8-tetramethyl-2-naphthyl)-3-methoxy propenyl] phenylsulfone To a suspension of 1 g of methyl 4-[E3-(5,6,7,8-tetrahydro-5,5,8,8-tetramethyl-2-naphthyl)-3-oxo propenyl] phenylsulfone, obtained in Example V, in 80 cm³ of methanol, stirred in the absence of light at 0° C., there is added all at once, 0.1 g of sodium borohydride. Stirring is maintained for 4 hours at this temperature, then the methanol is removed by evaporation under reduced pressure. The resulting crude product is taken up in 200 cm³ of water and the suspension is extracted three times with 100 cm³ of ethyl acetate. The ethyl acetate phases are combined, washed with a saturated aqueous solution of ammonium chloride, dried on magnesium sulfate and concentrated under reduced pressure.

0.5 g of crude methyl 4-[E3-(5,6,7,8-tetrahydro-5,5,8,8-tetramethyl-2-naphthyl)-3-hydroxy propenyl] phenylsulfone is recovered and then dissolved in 30 cm³ of methanol in the presence of paratoluene sulfonic acid as a catalyst. The solution is heated at reflux for 2 hours in the absence of light. The methanol is evaporated under reduced pressure and the crude product is purified by passage through a silica gel chromatography column. The expected methyl ether is eluted with a 8/2 heptane/ethyl acetate mixture then, after evaporation of the eluant, recrystallized in hexane.

0.3 g of methyl 4-[E3-(5,6,7,8-tetrahydro-5,5,8,8-tetramethyl-2-naphthyl)-3-methoxy propenyl] phenylsulfone in the form of white crystals whose melting point is 104° C. is obtained.

Elemental analysis: $C_{25}H_{32}O_3S$

|  | C | H | O | S |
|---|---|---|---|---|
| Calculated | 72.77 | 7.82 | 11.63 | 7.77 |
| Found | 72.38 | 8.09 | 12.02 | 7.50 |

EXAMPLE XIV

Preparation of ethyl 6-[(5,6,7,8-tetrahydro-5,5,8,8-tetramethyl-2-naphthyl) carbonyl] 2-naphthylsulfone To a solution, stirred in the absence of the humidity of the air, of 1 g of 6-ethylsulfonyl-2-naphthalene carboxylic acid chloride, prepared in accordance with Example D above, in 70 cm³ of anhydrous 1,2-dichloroethane, there is added 0.75 g of 1,2,3,4-tetrahydro-1,1,4,4-tetramethyl naphthalene, then at 0° C., in small amounts, 0.75 g of aluminum chloride.

At the end of the addition, stirring is maintained again for one hour at ambient temperature. The reaction mixture is then poured into 100 cm³ of a saturated aqueous solution of ammonium chloride, then extracted three times with 100 cm³ of methylene chloride. The combined organic phases are washed with sodium bicarbonate, then with water, dried on magnesium sulfate and concentrated.

The crude product is recrystallized in a hexane/isopropyl ether mixture. 0.9 g of ethyl 6-[(5,6,7,8-tetrahydro-5,5,8,8-tetramethyl-2-naphthyl) carbonyl]-2-naphthylsulfone in the form of white crystals whose melting point is 145° C. is obtained.

Elemental analysis: $C_{27}H_{30}O_3S$

|  | C | H | O | S |
|---|---|---|---|---|
| Calculated | 74.62 | 6.96 | 11.04 | 7.38 |
| Found | 73.95 | 7.00 | 11.78 | 7.06 |

EXAMPLE XV

Preparation of ethyl 6-[(1,1,2,3,3-pentamethyl-5-indanyl) carbonyl] 2-naphthylsulfone To a mixture, stirred at 0° C. in the absence of the humidity of the air, of 1.1 g of 1,1,2,3,3-pentamethyl indane and 1.5 g of 6-ethylsulfonyl-2-naphthalene carboxylic acid chloride, obtained in accordance with Example D above, in 70 cm³ of anhydrous 1,2-dichloroethane, there are added, in small portions, 1.1 g of aluminum chloride. After the end of the addition, the mixture is stirred for one hour at 0° C., then for one hour at ambient temperature. The mixture is then poured into 100 cm³ of a saturated solution of ammonium chloride, and extracted three times with 100 cm³ of dichloromethane. The organic phases are combined, washed with sodium bicarbonate, then with water and finally dried on magnesium sulfate. After evaporation of the solvent, 1.5 g of a crude product are obtained which is then recrystallized in a 1/1 hexane/toluene mixture containing a trace of ethanol.

The ethyl 6-[(1,1,2,3,3-pentamethyl-5-indanyl) carbonyl] 2-naphthylsulfone is a white powder whose melting point is 136° C.

Elemental analysis: $C_{27}H_{30}O_3S$

|  | C | H | O | S |
|---|---|---|---|---|
| Calculated | 74.62 | 6.96 | 11.04 | 7.38 |
| Found | 74.42 | 6.95 | 11.06 | 7.45 |

EXAMPLE XVI

Preparation of ethyl 6-[(5,6,7,8-tetrahydro-5,5,8,8-tetramethyl-2-naphthyl) hydroxymethyl]-2-naphthylsulfone To a suspension of 200 mg of ethyl 6-[(5,6,7,8-tetrahydro-5,5,8,8-tetramethyl-2-naphthyl) carbonyl]-2-naphthylsulfone, obtained in accordance with Example XIV, in 30 cm³ of methanol cooled to 0° C., there are added 100 mg of sodium borohydride. The reaction mixture is maintained under stirring for 30 minutes, then it is returned to ambient temperature. After verification by thin layer chromatography of the disappearance of the starting carbonyl product, the alcohol is evaporated under reduced pressure and the residue is taken up in 100 cm³ of water and acidified with a solution of 1N HCl. The resulting precipitate is filtered and dried under a vacuum.

After recrystallization in a toluene/hexane mixture, 150 mg of white crystals melting at 157° C. are recovered and whose NMR$^1$H 80 MHz spectrum conforms to the expected structure.

Elemental analysis: $C_{27}H_{32}O_3S$

|  | C | H | O | S |
|---|---|---|---|---|
| Calculated | 74.27 | 7.39 | 11.00 | 7.34 |
| Found | 74.10 | 7.35 | 11.19 | 7.44 |

EXAMPLE XVII

Preparation of ethyl 6-[1-(5,6,7,8-tetrahydro-5,5,8,8-tetramethyl-2-naphthyl)-1-hydroxyethyl]-2-naphthylthioether To a solution of 6.9 g of 2-bromo-5,6,7,8-tetrahydro-5,5,8,8-tetramethyl naphthalene in 50 cm$^3$ of anhydrous tetrahydrofuran, there is added 0.75 g of magnesium. The preparation of the organomagnesium is started by local heating, then the solution is maintained at reflux of THF until the complete consumption of the magnesium.

The reaction medium is then cooled to 0° C., and there are slowly added 3 g of 2-acetyl-6-ethylthio naphthalene, obtained in accordance with Example C(2), in solution in 50 cm$^3$ of THF. At the end of the addition, the reaction mixture is maintained at 0° C. for 2 hours, then at ambient temperature overnight. After verification by thin layer chromatography of the disappearance of the starting product, the reaction mixture is poured into 200 cm$^3$ of water and extracted with ethyl ether. The organic phase is washed with 100 cm$^3$ of a solution of sodium bicarbonate, then with water. After concentration under reduced pressure, 3.6 g of a yellow oil are recovered and which crystallized in hexane. After recrystallization in hexane, 2 g of the expected product whose melting point is 122° C. are obtained.

Elemental analysis: $C_{28}H_{34}OS$

|  | C | H | O | S |
|---|---|---|---|---|
| Calculated | 80.33 | 8.19 | 3.82 | 7.66 |
| Found | 80.33 | 8.26 | 4.60 | 7.67 |

EXAMPLE XVIII

Preparation of ethyl 6-[1-(5,6,7,8-tetrahydro-5,5,8,8-tetramethyl-2-naphthyl))ethenyl]-2-naphthylthioether To a solution of 1.6 g of ethyl 6-[1-(5,6,7,8-tetrahydro-5,5,8,8-tetramethyl-2-naphthyl)-1-hydroxyethyl]-2-naphthylthioether, obtained in accordance with Example XVII, in 100 cm$^3$ of toluene, there is added 1 g of paratoluene sulfonic acid. The reaction mixture is maintained under stirring for 1 hour at 70° C. and left to stand overnight at ambient temperature. After hydrolysis with 200 cm$^3$ of water, the expected product is extracted with ethyl acetate. The organic phase is washed with a solution of sodium bicarbonate, dried on magnesium sulfate, then concentrated under reduced pressure. After purification by silica gel chromatography (eluant: 9.5/05 heptane/ethyl acetate) 500 mg of a yellow oil are recovered that crystallizes in hexane and has a melting point of 102° C.

Elemental analysis: $C_{28}H_{32}S$

|  | C | H | S |
|---|---|---|---|
| Calculated | 83.94 | 8.05 | 8.01 |
| Found | 84.09 | 8.11 | 7.85 |

EXAMPLE XIX

Preparation of ethyl 6-[(5,8-dimethyl-6-methoxy-2-naphthyl) carbonyl]-2-naphthylsulfone A suspension of 3 g (11.35 mmoles) of 6-ethylsulfonyl naphthalene carboxylic acid, described in Example D, in 8.5 cm$^3$ (10 eq.) of thionyl chloride is heated for 1 hour at reflux. The resulting solution is evaporated to dryness at reduced pressure. The crude acid chloride thus isolated (beige solid) is taken up in 30 cm$^3$ of dry 1,2-dichloroethane. There are added 2.12 g (11.38 mmoles) of 5,8-dimethyl-6-methoxy naphthalene, and then, by portions, 2.27 g (17 mmoles) of anhydrous aluminum chloride. The mixture is stirred for 3 hours at ambient temperature. The reaction mixture is then poured into 30 cm$^3$ of ice water and diluted with 50 cm$^3$ of dichloroethane. The organic phase is decanted and the aqueous phase is reextracted with 30 cm$^3$ of dichloroethane. The organic phases are combined, washed with water, dried on sodium sulfate and evaporated to dryness. The isolated crude solid is purified by silica 60 gel chromatography in dichloromethane, followed by recrystallization in a toluene/hexane mixture. After drying, 1.5 g of pale yellow crystals of ethyl 6-[(5,8-dimethyl-6-methoxy-2-naphthyl) carbonyl]-2-naphthylsulfone whose melting point is 164°–165° C. are obtained.

The NMR$^1$H 250 MHz spectrum conforms to the expected structure.

Elemental analysis: $C_{26}H_{24}O_4S$

|  | C | H | O | S |
|---|---|---|---|---|
| Calculated | 72.20 | 5.59 | 14.80 | 7.41 |
| Found | 72.36 | 5.58 | 14.36 | 7.03 |

EXAMPLE XX

Preparation of ethyl 6-[(5,8-dimethyl-6-methoxy-2-naphthyl) hydroxymethyl]-2-naphthylsulfone To a solution of 0.5 g (1.16 mmoles) of ethyl 6-[(5,8-dimethyl-6-methoxy-2-naphthyl) carbonyl]-2-naphthysulfone, described in Example XIX, there is added 0.175 g (4.64 mmoles) of sodium borohydride. The mixture is stirred for 3 hours at ambient temperature. It is then cooled to 0° C., acidified by the slow addition of 0.1N HCl and extracted with ethyl ether (3×40 cm$^3$). The ether phase is washed with water, dried on sodium sulfate and evaporated to dryness. The isolated crude solid is purified by silica 60 gel chromatography in dichloromethane, followed by recrystallization in hexane containing a trace of acetone. After drying, 0.3 g of ethyl 6-[(5,8-dimethyl-6-methoxy-2-naphthyl) hydroxymethyl]-2-naphthylsulfone in the form of beige crystals whose melting point is 141°–143° C. is obtained.

The NMR$^1$H 250 MHz spectrum conforms to the expected structure.

Elemental analysis: $C_{26}H_{26}O_4S$

|            | C     | H    | O     | S    |
|------------|-------|------|-------|------|
| Calculated | 71.86 | 6.03 | 14.73 | 7.38 |
| Found      | 71.55 | 6.43 | 14.44 | 6.99 |

EXAMPLE XXI

Preparation of ethyl 6-[(5,8-dimethyl-6-methoxy-2-naphthyl) methylene]-2-naphthylsulfone A suspension of 0.43 g (1 mmole) of ethyl 6-[(5,8-dimethyl-6-methoxy-2-naphthyl) carbonyl]-2-naphthylsulfone, described in Example XIX, 10 cm³ of glacial acetic acid and 0.65 g of zinc powder (10 mmoles), is heated at reflux with stirring. There is then slowly added 0.85 cm³ (10 mmoles) of 12N HCl and reflux is maintained for 1 hour. There is again added 0.85 cm³ of 12N HCl and the mixture is stirred for 1 hour, while letting the reaction mixture cool. After the addition of 20 cm³ of 12N HCl, it is extracted with ether (3×30 cm³), washed with water, dried on sodium sulfate and evaporated to dryness. The crude yellow solid is rapidly purified by silica 60 gel chromatography (eluant: dichloromethane), followed by recrystallization in a hexane/acetone mixture. After drying, 160 mg of white needles of ethyl 6-[(5,8-dimethyl-6-methoxy-2-naphthyl) methylene]-2-naphthylsulfone whose melting point is 166° C. are obtained.

The NMR¹H 80 MHz spectrum conforms to the expected structure.

EXAMPLE XXII

Preparation of ethyl 6-[(5,6,7,8-tetrahydro-5,5,8,8-tetramethyl-2-naphthyl) methylene]-2-naphthylsulfone A suspension of 0.50 g of ethyl 6-[(5,6,7,8-tetrahydro-5,5,8,8-tetramethyl-2-naphthyl) carbonyl]-2-naphthylsulfone, described in Example XIV, in 10 cm³ of glacial acetic acid and 0.65 g of powdered zinc is heated at reflux with stirring for 1 hour. There is then slowly added 0.9 cm³ of concentrated HCl. Reflux is again maintained for one hour after the end of the addition of the HCl and there is again added 0.9 cm³ HCl. The mixture is then brought for one hour again to the boiling temperature of acetic acid and then left to stand overnight. The next day the reaction mixture is poured into 20 cm³ of 6N HCl and extracted three times with 30 cm³ of ethyl ether. The combined ether phases are washed with water, decanted and dried on sodium sulfate. After evaporation of the solvent 0.5 g of yellow powder is obtained which is then dissolved in methylene chloride. The solution is deposited on a silica gel chromatography column. After concentration of the fractions containing the pure expected product and drying, 0.32 g of ethyl 6-[(5,6,7,8-tetrahydro-5,5,8,8-tetramethyl-2-naphthyl) methylene]-2-methylsulfone in the form of white crystals whose melting point is 174° C. is obtained.

The NMR¹H spectrum corresponds to the expected structure.

Examples of Compositions

A. Oral Compositions

Example 1—0.2 g tablet

| Ethyl 6-[(5,6,7,8-tetrahydro-5,5,8,8-tetramethyl-2-naphthyl) carbonyl]-2-naphthylsulfone | 0.010 g |
|---|---|
| Starch | 0.115 g |
| Dicalcium phosphate | 0.020 g |
| Silica | 0.020 g |
| Lactose | 0.030 g |
| Talc | 0.010 g |
| Magnesium stearate | 0.005 g |

Example 2—Drinkable suspension in 5 ml ampoules

| Ethyl 6-[(1,1,2,3,3-pentamethyl-5-indanyl) carbonyl]-2-naphthyl sulfone | 0.010 g |
|---|---|
| Glycerine | 0.500 g |
| Sorbitol, 70% | 0.500 g |
| Sodium saccharinate | 0.010 g |
| Methyl parahydroxy benzoate | |
| Flavoring agent, sufficient amount | |
| Purified water, sufficient amount | |

B. Topical Compositions

Example 3—Ointment

| Ethyl 6-[(5,6,7,8-tetrahydro-5,5,8,8-tetramethyl-2-naphthyl) carbonyl]-2-naphthylsulfone | 0.010 g |
|---|---|
| Fluid petrolatum oil | 9.100 g |
| Silica, sold under the trade name "Aerosil 200" by Degussa | 9.100 g |
| Isopropyl myristate, sufficient amount for | 100.00 g |

Example 4—Anionic oil-in-water cream

| Ethyl 6-[(1,1,2,3,3-pentamethyl-5-indanyl) carbonyl]-2-naphthyl sulfone | 0.100 g |
|---|---|
| Sodium dodecyl sulfate | 0.800 g |
| Glycerol | 2.000 g |
| Stearyl alcohol | 20.000 g |
| Triglycerides of capric/caprylic acids, sold under the trade name "Miglyol 812" by Dynamit Nobel | 20.000 g |
| Preservatives, sufficient amount | |
| Demineralized water, sufficient amount for | 100.000 g |

Example 5—Gel

| Ethyl 6-[(1,1,2,3,3-pentamethyl-5-indanyl) carbonyl]-2-naphthyl sulfone | 0.500 g |
|---|---|
| Hydroxypropyl cellulose, sold under the trade name "Klucel HF" by Hercules | 2.000 g |
| Water/ethanol, 50/50, sufficient amount for | 100.000 g |

In this Example, the active compound can be replaced by 0.05 g of ethyl 6-[(5,6,7,8-tetrahydro-5,5,8,8- tetramethyl-2-naphthyl) hydroxymethyl]-2-naphthyl-sulfone.

Example 6—Anti-seborrhea cream

| | |
|---|---|
| Polyoxyethylenated stearate (40 moles) of ethylene oxide), sold under the trade name "Myrj 52" by Atlas | 4.000 g |
| Mixture of lauryl esters of sorbitol and sorbitan, polyoxyethylenated with 20 moles of ethylene oxide, sold under the trade name "Tween 20" by Atlas | 1.800 g |
| Mixture of glycerol mono- and di-stearate, sold under the trade name "Geleol" by Gattefosse | 4.200 g |
| Propylene glycol | 10.000 g |
| Butylhydroxyanisole | 0.010 g |
| Butylhydroxytoluene | 0.020 g |
| Cetyl-stearyl alcohol | 6.200 g |
| Preservatives, sufficient amount | |
| Perhydrosqualene | 18.000 g |
| Mixture of caprylic/capric triglycerides, sold under the trade name "Miglyol 812" by Dynamit Nobel | 4.000 g |
| S-carboxymethyl cysteine | 3.000 g |
| Triethanolamine, 99% | 2.500 g |
| Methyl 4-[E3-(1,1,2,3,3-pentamethyl-5-indanyl)-3-hydroxy propenyl] phenylsulfone | 0.100 g |
| Water, sufficient amount for | 100.000 g |

Example 7—Anti-seborrhea cream

| | |
|---|---|
| Polyoxyethylenated stearate (40 moles) of ethylene oxide) sold under the trade name "Myrj 52" by Atlas | 4.000 g |
| Mixture of lauryl esters of sorbitol and sorbitan polyoxyethylenated with 20 moles of ethylene oxide, sold under the trade name "Tween 20" by Atlas | 1.800 g |
| Mixture of glycerol mono- and di-stearate, sold under trade name "Geleol" by Gattefosse | 4.200 g |
| Propyleneglycol | 10.000 g |
| Butylhydroxyanisole | 0.010 g |
| Butylhydroxytoluene | 0.020 g |
| Cetyl-stearyl alcohol | 6.200 g |
| Preservatives, sufficient amount | |
| Perhydrosqualene | 18.000 g |
| Mixture of caprylic/capric triglycerides, sold under the trade name "Miglyol 812" by Dynamit Nobel | 4.000 g |
| 5-amino-5-carboxy-3-thio pentanoate of 2-benzylthio ethyl ammonium | 3.000 g |
| Ethyl 6-[(5,6,7,8-teterahydro-5,5,8,8-tetramethyl-2-naphthyl) carbonyl]-2-naphthylsulfone | 0.500 g |
| Water, sufficient amount for | 100.00 g |

Example 8—Hair lotion

| | |
|---|---|
| Propylene glycol | 20.000 g |
| Ethanol | 34.870 g |
| Polyethylene glycol, molecular mass 400 | 40.000 g |
| Water | 4.000 g |
| Butylhydroxyanisole | 0.010 g |
| Butylhydroxytoluene | 0.020 g |
| Ethyl 6-[(5,6,7,8-tetrahydro-5,5,8,8-tetramethyl-2-naphthyl) carbonyl]-2-naphthylsulfone | 0.100 g |
| Minoxidil | 1.000 g |

Example 9—Anti-acne gel

| | |
|---|---|
| Ethyl 6-[(5,6,7,8-tetrahydro-5,5,8,8-tetramethyl-2-naphthyl) carbonyl]-2-naphthylsulfoxide | 0.100 g |
| Isopropyl alcohol | 40.000 g |
| Acrylic acid polymer, sold under the trade name "Carbopol 940" by Goodrich Chemical Company | 1.000 g |
| Triethanolamine, 99% | 0.600 g |
| Butylhydroxyanisole | 0.010 g |
| Butylhydroxytoluene | 0.020 g |
| Tioxolone | 0.500 g |
| Propyleneglycol | 8.000 g |
| Purified water, sufficient amount for | 100.000 g |

What is claimed is:

1. An aromatic polycyclic compound having the formula

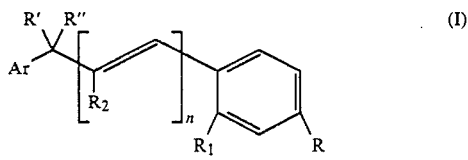

wherein

R represents —SO$_2$R$_3$,

R$_3$ represents linear or branched lower alkyl, monohydroxyalkyl, polyhydroxyalkyl, aminoalkyl, carboxyalkyl, aminocarboxyalkyl or alkoxyalkyl, R' represents hydrogen, lower alkyl, lower alkoxy, hydroxy, C$_1$-C$_4$ acyloxy or amino, R" represents hydrogen, lower alkyl or lower alkoxy, or R' and R", taken together, form an oxo, methano or hydroxyimino radical, n=1, R$_1$ and R$_2$, taken together form a vinylene radical and Ar represents an aromatic radical selected from the group consisting of:

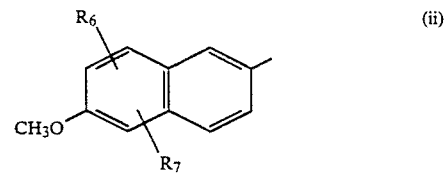

and

-continued

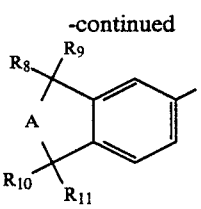
(iii)

wherein $R_4$, $R_5$, $R_6$, $R_7$, $R_8$, $R_9$, $R_{10}$ and $R_{11}$ represent hydrogen or lower alkyl, at least one of $R_4$ and/or $R_5$ being other than hydrogen, and at least two of $R_8$–$R_{11}$ being other than hydrogen, A represents methylene or dimethylene unsubstituted or substituted by lower alkyl; when A represents dimethylene, $R_8$ and $R_{10}$ together can form methylene or dimethylene, and the salts of the compound of formula I or its optical and geometric isomers.

2. The compound of claim 1 selected from the group consisting of ethyl 6-[(5,6,7,8-tetrahydro-5,5,8,8-tetramethyl-2-naphthyl) carbonyl]-2-naphthylsulfone, ethyl 6-[(1,1,2,3,3-pentamethyl-5-indanyl) carbonyl]-2-naphthylsulfone, ethyl 6-[(1,1,3,3-tetramethyl-5-indanyl) carbonyl]-2-naphthylsulfone, 2′,3′-dihydroxypropyl 6-[(5,6,7,8-tetrahydro-5,5,8,8-tetramethyl-2-naphthyl) carbonyl]-2-naphthylsulfone, ethyl 6-[(5,6,7,8-tetrahydro-5,5,8,8-tetramethyl-2-naphthyl) hydroxymethyl]-2-naphthylsulfone, ethyl 6-[(5,8-methano-5,6,7,8-tetrahydro-2-naphthyl) carbonyl]-2-naphthylsulfone, ethyl 6-[(5,6,7,8-tetrahydro-5,5,8,8-tetramethyl-2-naphthyl) methylene]-2-naphthylsulfone, ethyl 6-[1-(5,6,7,8-tetrahydro-5,5,8,8-tetramethyl-2-naphthyl)-1-hydroxyethyl]-2-naphthylsulfone, ethyl 6-[(5,8-dimethyl-6-methoxy-2-naphthyl) carbonyl]-2-naphthylsulfone, ethyl 6-[(5,8-dimethyl-6-methoxy-2-naphthyl) hydroxymethyl]-2-naphthylsulfone, and ethyl 6-[(5,8-dimethyl-6-methoxy-2-naphthyl) methylene]-2-naphthyl sulfone.

3. The compound of claim 1 which is ethyl 6-[(5,6,7,8-tetrahydro-5,5,8,8-tetramethyl-2-naphthyl) carbonyl]2-naphthylsulfone.

* * * * *